United States Patent [19]

Dahms

[11] Patent Number: 5,747,012
[45] Date of Patent: May 5, 1998

[54] COMPOSITIONS CONTAINING SUNSCREENS

[75] Inventor: Gerd Herbert Dahms, Velbert, Germany

[73] Assignee: Tioxide Specialties Limited, London, England

[21] Appl. No.: 725,552

[22] Filed: Oct. 3, 1996

Related U.S. Application Data

[63] Continuation of Ser. No. 258,286, Jun. 10, 1994, abandoned.

[30] Foreign Application Priority Data

Jun. 11, 1993 [DE] Germany .......................... 9312045 U

[51] Int. Cl.$^6$ ..................................................... A61K 7/44
[52] U.S. Cl. ................................. 424/60; 424/63; 424/69
[58] Field of Search ............................... 424/59, 60, 63, 424/69

[56] References Cited

U.S. PATENT DOCUMENTS

| | | | |
|---|---|---|---|
| 4,731,242 | 3/1988 | Palinczar | 424/59 |
| 4,820,508 | 4/1989 | Wortzman | 424/59 |
| 4,917,883 | 4/1990 | Strobridge | 424/59 |
| 4,927,464 | 5/1990 | Cowie | 106/436 |
| 5,028,417 | 7/1991 | Bhat et al. | 424/59 |
| 5,032,390 | 7/1991 | Iwaya | 424/59 |
| 5,041,281 | 8/1991 | Strobridge | 424/59 |
| 5,093,109 | 3/1992 | Mausner | 424/59 |
| 5,169,624 | 12/1992 | Ziegler et al. | 424/59 |
| 5,208,012 | 5/1993 | Sudo et al. | 424/59 |
| 5,215,749 | 6/1993 | Nicoll | 424/401 |
| 5,250,289 | 10/1993 | Boothroyd et al. | 424/59 |

FOREIGN PATENT DOCUMENTS

| | | |
|---|---|---|
| 1602592 | 11/1992 | Australia . |
| 1602692 | 11/1992 | Australia . |
| 0456458 | 11/1991 | European Pat. Off. . |
| 0456459 | 11/1991 | European Pat. Off. . |
| 0456460 | 11/1991 | European Pat. Off. . |
| 2264703 | 9/1993 | European Pat. Off. . |
| 49-00450 | 1/1974 | Japan . |
| 5272833 | 6/1977 | Japan . |
| 53-124627 | 10/1978 | Japan . |
| 58-043912 | 3/1983 | Japan . |
| 58-062106 | 4/1983 | Japan . |
| 59-062517 | 4/1984 | Japan . |
| 60-149515 | 7/1985 | Japan . |
| 60-149516 | 7/1985 | Japan . |
| 60-149517 | 7/1985 | Japan . |
| 1030637 | 1/1989 | Japan . |
| 50-25028 | 2/1993 | Japan . |
| 2205088 | 11/1988 | United Kingdom . |
| 2205239 | 12/1988 | United Kingdom . |
| 2206339 | 1/1989 | United Kingdom . |
| 2217987 | 11/1989 | United Kingdom . |
| 2226018 | 6/1990 | United Kingdom . |
| 2264487 | 9/1993 | United Kingdom . |
| WO9006103 | 6/1990 | WIPO . |
| WO9009777 | 9/1990 | WIPO . |
| WO9011067 | 10/1990 | WIPO . |
| WO9217159 | 10/1992 | WIPO . |
| WO9307854 | 4/1993 | WIPO . |
| WO9311742 | 6/1993 | WIPO . |
| WO9415580 | 7/1994 | WIPO . |

*Primary Examiner*—C Warren Ivy
*Assistant Examiner*—Evelyn Huang
*Attorney, Agent, or Firm*—Baker & Botts, LLP

[57] ABSTRACT

A process for preparing a composition suitable for topical application to human skin is disclosed. The process comprises mixing particles of metallic oxide dispersed in oil and having a primary particle size less than 0.2 micrometer with one or more emulsifiers, an aqueous phase and a hydrophilic organic sunscreen so as to prepare an emulsion. The composition contains up to 10 percent by weight metallic oxide and up to 7 percent by weight hydrophilic organic sunscreen. The emulsions are useful as sunscreen compositions, skin protectants, moisturisers, and after-sun lotions. The measured Sun Protection Factor for a composition of the invention is considerably higher than would be expected from a knowledge of the individual UV absorbing characteristics of the metallic oxide and the hydrophilic organic sunscreen.

28 Claims, No Drawings

COMPOSITIONS CONTAINING SUNSCREENS

This application is a continuation of application Ser. No. 08/258,286, filed Jun. 10, 1994 abandoned.

The invention relates to compositions for application to human skin and particularly to compositions containing a combination of inorganic and organic sunscreens.

The use of inorganic oxides which have a particle size such that they are substantially transparent to visible light but reflect or absorb UV light to provide sunscreen compositions is known. However, in order to produce a sunscreen composition having a high sun protection factor (SPF) it is sometimes necessary to use relatively large amounts of such oxides and this can lead to undesirable visible tinting due to the small absorbance of visible light.

A combination of an inorganic oxide and an organic sunscreen can be used to obtain a high SPF with a relatively small amount of inorganic oxide but physiological damage to the body can occur following topical application of organic sunscreens in effective concentrations and consequently safety limits have been imposed on the quantity which is permitted in a composition for topical application.

It is therefore desirable to produce compositions which optimise the effectiveness of compounds used as UV absorbers and it is an object of this invention to provide a method of preparing compositions which improve the effectiveness of a combination of inorganic and organic UV absorbers and in which compositions the amount of organic UV absorber is minimised.

According to the invention a process for the preparation of a composition suitable for topical application to human skin comprises mixing a dispersion in an oil of particles of a metallic oxide having an average primary particle size of less than 0.2 micrometer with one or more emulsifiers and an aqueous phase under conditions in which an emulsion is formed and with a hydrophilic organic sunscreen wherein the composition contains up to 10 percent by weight metallic oxide and up to 7 percent by weight hydrophilic organic sunscreen.

Compositions prepared according to the process of the invention have been shown to possess an SPF which is considerably greater than would be expected by calculating an SPF based on the additive effect of the metallic oxide and the organic sunscreen.

The emulsion which is formed by the process of the invention can be an oil-in-water emulsion or a water-in-oil emulsion and the skilled person will readily be able to adjust the composition and the conditions under which it is prepared to produce either type of emulsion.

Preferably the metallic oxide used in the process of the invention comprises an oxide of titanium, zinc or iron and most preferably the metallic oxide is titanium dioxide.

The average primary particle size of the particles of metallic oxide used in the process of the invention is less than 0.2 micrometer and where the particles are substantially spherical then this size will be taken to represent the diameter. However, the invention also encompasses particles of metallic oxides which are non-spherical and in such cases the average primary particle size refers to the largest dimension.

Preferably the average primary particle size of the particles is from 0.01 to 0.15 micrometer and more preferably from 0.01 to 0.06 micrometer when they are substantially spherical. Particularly useful products can be prepared using substantially spherical particles having an average primary particle size in the range 0.01 to 0.03 micrometer. For particles having an acicular shape the average largest dimension of the primary particles is preferably less than 0.15 micrometer and more preferably from 0.02 to 0.10 micrometer.

When the metallic oxide is titanium dioxide the particles are preferably acicular in shape and have a ratio of largest dimension to shortest dimension of from 8:1 to 2:1.

When the metallic oxide is zinc oxide the particles preferably have an average primary particle size of 0.005 to 0.15 micrometer and more preferably have an average primary particle size of 0.03 to 0.07 micrometer.

The particles of metallic oxide may comprise substantially pure metallic oxide but may also carry an inorganic coating or organic coating. For example, particles of titanium dioxide can be coated with oxides of other elements such as oxides of aluminium, zirconium or silicon and a form of acicular, coated titanium dioxide which is especially useful in the process of this invention is disclosed in UK Patent GB 2 205 088.

The particles of metallic oxides may also carry, if desired, a coating of one or more organic materials such as polyols, amines, alkanolamines, polymeric organic silicon compounds, hydrophilic polymers such as polyacrylamide, polyacrylic acid, carboxymethyl cellulose and xanthan gum or surfactants.

The metallic oxide is used in the process of the invention in a quantity sufficient to ensure a concentration of up to 10 weight percent with respect to the final emulsion. When the metallic oxide is titanium dioxide, it is preferably present in an amount of from 1 to 6 percent by weight and most preferably it is present in an amount of from 4 to 5 percent by weight. When the metallic oxide is zinc oxide, the preferred amount is from 3 to 8 percent by weight and the most preferred amount is from 5 to 7 percent by weight.

In carrying out the process of the invention a dispersion of a particulate metallic oxide in an oil having a primary particle size as hereinbefore defined is used. Typically, the dispersion is prepared by milling the metallic oxide in the oil in the presence of a particulate grinding medium and in the presence of a dispersing agent.

UK Patent GB 2 206 339 discloses a dispersion in oil of titanium dioxide having an average particle size of from 0.01 to 0.15 micrometer containing an organic dispersing agent. The dispersions described in GB 2 206 339 are particularly suitable for use in the process of the current invention when it is desired to produce an emulsion containing titanium dioxide.

The technique described in GB 2 206 339 can be used to prepare dispersions in oil of metallic oxides other than titanium dioxide which are suitable for use in the process of the invention.

Suitable dispersing agents which can be used to prepare dispersions of metallic oxides include those disclosed in GB 2 206 339 such as dispersing agents having the formula X.CO.AR in which A is a divalent bridging group, R is a primary, secondary or tertiary amino group or a salt thereof with an acid or a quaternary ammonium salt group and X is the residue of a polyester chain which together with the —CO— group is derived from a hydroxy carboxylic acid of the formula $HOR^1COOH$ in which $R^1$ represents a saturated or unsaturated hydrocarbyl group. Typical dispersing agents are based on ricinoleic acid, hydroxystearic acid and hydrogenated castor oil fatty acid.

Dispersing agents based on one or more polyesters or salts of a hydroxy carboxylic acid or a carboxylic acid free of hydroxy groups can also be used. Other suitable dispersing agents are those monoesters of fatty acid alkanolamides and carboxylic acids and their salts based on $C_6$ to $C_{22}$ saturated or unsaturated fatty acids. For example, alkanolamides can be based on ethanolamine, propanolamine or aminoethyl ethanolamine. Alternative dispersing agents are those based on polymers or copolymers of acrylic or methacrylic acids, or dispersing agents having ethoxy groups in the constituent radical such as those based on ethoxylated phosphate esters.

GB 2 206 339 is related to dispersions containing greater than 40 percent by weight titanium dioxide. However, the techniques disclosed in GB 2 206 339 are generally applicable to dispersions containing a range of concentrations of metallic oxides. Dispersions prepared using these techniques and containing from 40 percent to 70 percent by weight metallic oxide are suitable for use in the process of this invention. Preferably, the dispersion of metallic oxide in an oil has a concentration in the range 40 percent to 60 percent metallic oxide by weight of the dispersion.

The hydrophilic organic sunscreens which are of use in the current invention are organic compounds which have been shown to be useful when added to compositions for the purpose of absorbing UV light and which have a solubility in water at 20° C. of greater than 5 percent by weight. Specific examples of useful organic sunscreens are given in the following table, identified by their INCI name (formerly CTFA name) and, in some cases, other common names

| INCI NAME | OTHER COMMON NAME |
| --- | --- |
| Benzophenone-4 | Sulisobenzone |
| PABA | p-Aminobenzoic acid |
| TEA Salicylate | Triethanolamine salicylate |
| Phenylbenzimidazole sulphonic acid | Novantisol |
| DEA Methoxy cinnamate | |

The preferred organic sunscreen is phenylbenzimidazole sulphonic acid.

A mixture of two or more hydrophilic organic sunscreens can be used.

The quantity of hydrophilic organic sunscreens used will depend to some extent upon the nature of the organic sunscreen but is up to 7 percent by weight based on weight of emulsion. Preferably the amount of hydrophilic sunscreen is from 1 to 6 percent by weight.

When the hydrophilic organic sunscreen is phenylbenzimidazole sulphonic acid the preferred quantity is from 2 to 5 percent by weight.

When the process of the invention is operated in a manner that produces an oil-in-water emulsion then suitable emulsifiers include both hydrophobic and hydrophilic materials. Suitable hydrophobic emulsifiers include fatty alcohols, fatty acids, glyceryl esters, sorbitan esters, methylglycoside esters and sucrose esters.

Hydrophilic emulsifiers suitable for use in forming an oil-in-water emulsion include polyoxyethylene sorbitan fatty acid esters, polyoxyethylene fatty acid esters, polyoxyethylene fatty ethers, phosphate esters, fatty alcohol sulphates, polyglycoside ethers and polyglycoside esters.

When it is desired to produce a water-in-oil emulsion then an embodiment of the process of the invention can be based on the process described in the pending application filed in the United Kingdom under the application number GB 9301462.9. When this embodiment of the process of the invention is carried out then a water-in-oil emulsion is prepared containing a relatively small amount of emulsifiers by comparison with previously known emulsions. Preferably the amount of emulsifier used is less than 1% by weight of the emulsion when a non-polar oil phase is used. In the absence of a non-polar oil in the oil phase of the emulsion the amount of emulsifier is preferably from 1 to 2% by weight of emulsion.

Emulsifiers which are suitable for use in this embodiment include silicone-based emulsifiers, ethylene oxide/propylene oxide copolymers and lipid emulsifiers such as fatty alcohols, fatty acids, glyceryl esters, sorbitan esters, methylglycoside esters, sugar esters and alkoxylated derivatives of these alcohols, acids and esters. Many of these emulsifiers are easy to produce from renewable raw materials, are readily biodegradable and do not contain toxic side products.

In forming an oil-in-water emulsion or a water-in-oil emulsion according to the process of the invention an oil phase is employed. The components of this oil phase are oleophilic, cosmetically acceptable compounds. Examples of suitable compounds include paraffin oils, silicone oils, triglyceride esters and esters of fatty acids and fatty alcohols.

The dispersion of metallic oxide in oil, emulsifier and aqueous phase are mixed under conditions which produce an emulsion.

Typically, an oil-in-water emulsion is formed by initially mixing together the oleophilic components to form an oil phase. When a hydrophobic emulsifier is used this is added to the oil phase. The dispersion of metallic oxides in oil may also be added to the oil phase at this stage. The hydrophilic organic sunscreen is mixed with water, hydrophilic emulsifier or emulsifiers, and any other desired hydrophilic components to form an aqueous phase. If necessary, one or both of the phases are heated and the oil phase and aqueous phase are then mixed together to form an oil-in-water emulsion. The dispersion of metallic oxides in oil is added at this stage, if it has not been added previously to the oil phase.

A water-in-oil emulsion is usually formed by initially mixing the dispersion of metallic oxide in oil with the emulsifier or emulsifiers and, when desired, any other oleophilic components to form an oil phase. This oil phase is subsequently mixed with an aqueous phase to form a water-in-oil emulsion. Alternatively, the dispersion of metallic oxide can be mixed with an emulsion which has previously been prepared by mixing an oil phase containing emulsifier with an aqueous phase.

Such water-in-oil emulsions may be prepared at room temperature but it is preferred to use a temperature of at least 40° C. and, when components which are solid at room temperature are present, it is usually necessary to heat one or both phases before mixing.

The hydrophilic organic sunscreen is preferably added to the aqueous phase before this is mixed with the dispersion of metallic oxide in oil but it can also be mixed with the emulsion after this has been prepared from the dispersion of metallic oxide in oil and aqueous phase.

Other ingredients can be added to the emulsion and these ingredients may be introduced in any convenient manner. For example they can be mixed with the emulsion or added to the dispersion of metallic oxide in oil or the aqueous phase before these components are mixed together. As examples, perfumes, antioxidants, moisturisers, thickeners and preservatives are normally added to emulsions to produce a commercially acceptable cosmetic product.

The emulsions produced according to the process of this invention find use as sunscreen compositions, as skin protectants, as moisturisers and as after-sun lotions and generally have the property of being transparent to visible light but absorbent to UV light.

The measured SPF for an emulsion prepared according to the process of the invention is considerably higher than expected. For example, an emulsion containing 4 percent titanium dioxide and no organic sunscreen was shown to have an in-vitro SPF of 6. Previous experience indicates that the addition of 3 percent phenylbenzimidazole sulphonic acid (Trade Name Eusolex 232) to such a composition should increase the SPF to 12. In fact, an emulsion containing a combination of 4 percent titanium dioxide and 3 percent Eusolex 232 prepared according to the method of the invention has been found to have an SPF of greater than 15.

The invention is further illustrated by the following Examples.

EXAMPLE 1

An oil-in-water emulsion suitable for use as a sunscreen was prepared according to the following formulation

|   | | % by weight |
|---|---|---|
| 1) | Isopropyl Myristate | 4.00 |
| 2) | Paraffin Oil | 6.50 |
| 3) | Grape seed oil | 2.50 |
| 4) | Sorbitan Stearate | 3.00 |
|    | (sold under the Trade Name Span 60) | |
| 5) | Petrolatum | 2.00 |
| 6) | Sucrose Stearate | 3.00 |
|    | (sold under the Trade Name Grilloten PSE141 G) | |
| 7) | Disodium Ricinoleamido MEA-Sulfosuccinate | 0.20 |
|    | (sold under the Trade Name Rewoderm S1333) | |
| 8) | Glycerol | 4.00 |
| 9) | Allantoin | 0.20 |
| 10) | D-Panthenol | 0.80 |
| 11) | Phenylbenzimidazole sulphonic acid | 3.00 |
|    | (sold under the Trade Name Eusolex 232) | |
| 12) | Sodium Cetearyl Sulphate | 0.35 |
|    | (sold under the Trade Name Lanette E) | |
| 13) | Demineralised water | 60.05 |
| 14) | 40% by weight dispersion of titanium dioxide in octyl palmitate | 10.00 |
|    | (sold under the Trade Name Tioveil OP) | |
| 15) | Mixture of alkyl parabens in phenoxyethanol | 0.20 |
|    | (sold under the Trade Name Phenonip) | |
| 16) | Perfume | 0.20 |

Ingredients 1 to 5 were mixed to form an oil phase and heated to 80° C. Ingredients 6 to 13 were mixed to form an aqueous phase and heated to 80° C. The oil phase was added to the aqueous phase with high-speed stirring (Braun kitchen mixer type 4169). Ingredient 14 was then added, and high-speed stirring was continued for 1 minute to homogenize the mixture. The resulting emulsion was cooled to 25° C. in a water bath, with slow agitation. Ingredients 15 and 16 were then added with moderate stirring.

The product so formed had an in-vitro SPF of 21.6 (measured by the method of Diffey and Robson: J. Soc. Cosmet. Chem. 40, p.127–133 (1989)).

A product made according to the same composition, but omitting the phenylbenzimidazole sulphonic acid and substituting additional water, had an in-vitro SPF of 5.6.

EXAMPLE 2

An oil-in-water emulsion was prepared according to the following formulation:

|   | | % by weight |
|---|---|---|
| 1) | Isopropyl Myristate | 4.0 |
| 2) | Paraffin oil | 6.50 |
| 3) | Grape seed oil | 2.50 |

-continued

|   | | % by weight |
|---|---|---|
| 4) | Petrolatum | 2.00 |
| 5) | Sorbitan Stearate | 3.00 |
|    | (sold under the Trade Name Span 66) | |
| 6) | Sucrose Stearate | 3.00 |
|    | (sold under the Trade Name Grilloten PSE 141G) | |
| 7) | Disodium Ricinoleamido MEA-Sulfosuccinate | 0.20 |
|    | (sold under the Trade Name Rewoderm S1333) | |
| 8) | Glycerol | 4.00 |
| 9) | Allantoin | 0.20 |
| 10) | D-Panthenol | 0.80 |
| 11) | Benzophenone-4 | 1.00 |
|    | (sold under the Trade Name Uvinul MS40) | |
| 12) | Sodium Cetearyl Sulphate | 0.50 |
|    | (sold under the Trade Name Lanette E) | |
| 13) | Demineralised water | 61.90 |
| 14) | 40% by weight dispersion of titanium dioxide in octyl palmitate | 10.00 |
|    | (sold under the Trade Name Tioveil OP) | |
| 15) | Mixture of alkyl parabens in phenoxyethanol | 0.20 |
|    | (sold under the Trade Name Phenonip) | |
| 16) | Perfume | 0.20 |

Ingredients 1 to 5 were mixed to form an oil phase and heated to 80° C. Ingredients 6 to 13 were mixed to form an aqueous phase and heated to 80° C. The oil phase was added to the aqueous phase with high speed stirring (Braun mixer type 4169). Ingredient 14 was added, and high speed stirring was continued for one minute to homogenise the mixture. The resulting emulsion was cooled to 25° C. in a water bath, with slow agitation. Ingredients 15 and 16 were then added with moderate stirring.

The product so formed had an in-vitro SPF of 10.4 (measured by the method of Diffey and Robson: J. Soc. Cosmet. Chem. 40, p.127–133 (1989)).

A product made according to the same composition, but omitting the benzophenone-4 and substituting additional water, had an in-vitro SPF of 5.6. Addition of 1% benzophenone-4 would normally be expected to increase the SPF from 5.6 to approximately 8.0.

EXAMPLE 3

Oil-in-water emulsions were prepared according to the following formulations:

|   | | A % by weight | B % by weight | C % by weight |
|---|---|---|---|---|
| 1) | Isopropyl Myristate | 4.00 | 4.00 | 4.00 |
| 2) | Paraffin oil | 6.50 | 6.50 | 6.50 |
| 3) | Grape seed oil | 2.50 | 2.50 | 2.50 |
| 4) | Petrolatum | 2.00 | 2.00 | 2.00 |
| 5) | Sorbitan Stearate | 3.00 | 3.00 | 3.00 |
|    | (sold under the Trade Name Span 60) | | | |
| 6) | Sucrose Stearate | 3.00 | 3.00 | 3.00 |
|    | (sold under the Trade Name Grilloten PSE 141G) | | | |
| 7) | Glycerol | 4.00 | 4.00 | 4.00 |
| 8) | Allantoin | 0.20 | 0.20 | 0.20 |
| 9) | D-Panthenol | 0.80 | 0.80 | 0.80 |
| 10) | Benzophenone-4 | — | 3.00 | 3.00 |
|    | (sold under the Trade Name Uvinul MS40) | | | |
| 11) | Sodium Cetearyl Sulphate | 1.00 | 1.00 | 1.00 |
|    | (sold under the Trade Name Lanette E) | | | |
| 12) | Demineralised water | 62.60 | 69.60 | 59.60 |
| 13) | 40% by weight dispersion of titanium dioxide in octyl palmitate | 10.00 | — | 10.00 |

-continued

|  | A<br>% by<br>weight | B<br>% by<br>weight | C<br>% by<br>weight |
|---|---|---|---|
| (sold under the Trade Name Tioveil OP) | | | |
| 14) Mixture of alkyl parabens in phenoxyethanol (sold under the Trade Name Phenonip) | 0.20 | 0.20 | 0.20 |
| 15) Perfume | 0.20 | 0.20 | 0.20 |

Ingredients 1 to 5 were mixed to form an oil phase and heated to 80° C. Ingredients 6 to 12 (where included) were mixed to form an aqueous phase and heated to 80° C. The oil phase was added to the aqueous phase with high speed stirring (Braun mixer type 4169). Ingredient 13 was added, and high speed stirring was continued for one minute to homogenise the mixture. The resulting emulsion was cooled to 25° C. in a water bath, with slow agitation. Ingredients 14 and 15 were then added with moderate stirring.

The in-vitro SPF of each of the emulsions was measured using the method of Diffey and Robson: J. Soc. Cosmet. Chem., 40.p. 127-133 (1989).

The product A containing only titanium dioxide as active UV absorber had an in-vitro SPF of 7.2. The product B containing only benzophenone-4 as active UV absorber had an in-vitro SPF of 5.4. The product C containing both active UV absorbers had an in-vitro SPF of 20.1.

EXAMPLE 4

Oil-in-water emulsions were prepared according to the following formulations:

|  | D<br>% by<br>weight | E<br>% by<br>weight | F<br>% by<br>weight |
|---|---|---|---|
| 1) Isopropyl Myristate | 4.00 | 4.00 | 4.00 |
| 2) Paraffin oil | 6.50 | 6.50 | 6.50 |
| 3) Grape seed oil | 2.50 | 2.50 | 2.50 |
| 4) Petrolatum | 2.00 | 2.00 | 2.00 |
| 5) Sorbitan Stearate (sold under the Trade Name Span 60) | 3.00 | 3.00 | 3.00 |
| 6) Sucrose Stearate (sold under the Trade Name Grilloten PSE 141G) | 3.00 | 3.00 | 3.00 |
| 7) Glycerol | 4.00 | 4.00 | 4.00 |
| 8) Allantoin | 0.20 | 0.20 | 0.20 |
| 9) D-Panthenol | 0.80 | 0.80 | 0.80 |
| 10) Phenylbenzimidazole sulphonic acid (sold under the Trade Name Eusolex 232) | — | 3.00 | 3.00 |
| 11) Disodium ricinoleamido MEA-sulfosuccinate (sold under the Trade Name Rewoderm S1333) | 0.20 | 0.20 | 0.20 |
| 12) Demineralised water | 63.40 | 70.40 | 60.40 |
| 13) 40% by weight dispersion of titanium dioxide in a $C_{12-15}$ alkyl benzoate (sold under the Trade Name Tioveil FIN) | 10.00 | — | 10.00 |
| 14) Mixture of alkyl parabens in phenoxyethanol (sold under the Trade Name Phenonip) | 0.20 | 0.20 | 0.20 |
| 15) Perfume | 0.20 | 0.20 | 0.20 |

Ingredients 1 to 5 were mixed to form an oil phase and heated to 80° C. Ingredients 6 to 12 (where included) were mixed to form an aqueous phase and heated to 80° C. The oil phase was added to the aqueous phase with high speed stirring (Braun mixer type 4169). Ingredient 13 was added, and high speed stirring was continued for one minute to homogenise the mixture. The resulting emulsion was cooled to 25° C. in a water bath, with slow agitation. Ingredients 14 and 15 were then added with moderate stirring.

The in-vitro SPF of each of the emulsions was measured using the method of Diffey and Robson: J. Soc. Cosmet. Chem., 40, p127-133 (1989).

The product D containing only titanium dioxide as active UV absorber had an in-vitro SPF of 5.2. The product E containing only phenyl-benzimidazole sulphonic acid as UV absorber had an in-vitro SPF of 8.1. The product F containing both active UV absorbers had an in-vitro SPF of 21.7.

I claim:

1. A process for the preparation of a composition suitable for topical application to human skin comprising mixing a dispersion in an oil of particles of a metallic oxide having an average primary particle size of less than 0.2 micrometers with one or more emulsifiers and an aqueous phase under conditions in which an emulsion is formed and with a hydrophilic organic sunscreen wherein the composition contains up to 10 percent by weight metallic oxide and up to 7 percent by weight hydrophilic organic sunscreen.

2. A process according to claim 1 in which the metallic oxide is selected from the group consisting of oxides of titanium, zinc and iron.

3. A process according to claim 1 in which the metallic oxide particles are substantially spherical and have an average primary particle size from 0.01 to 0.15 micrometers.

4. A process according to claim 1 in which the metallic oxide particles are acicular and primary particles of the metallic oxide have an average largest dimension less than 0.15 micrometers.

5. A process according to claim 4 in which the metallic oxide is titanium dioxide and the particles thereof have a ratio of largest dimension to shortest dimension of from 8:1 to 2:1.

6. A process according to claim 1 in which the metallic oxide is zinc oxide and the particles thereof have an average primary particle size of 0.005 to 0.15 micrometers.

7. A process according to claim 1 in which the particles of metallic oxide carry an organic or an inorganic coating.

8. A process according to claim 1 in which the metallic oxide is titanium dioxide and is present in an amount of from 1 to 6 percent by weight with respect to weight of emulsion.

9. A process according to claim 1 in which the metallic oxide is zinc oxide and is present in an amount of from 3 to 8 percent by weight with respect to weight of emulsion.

10. A process according to claim 1 in which the hydrophilic organic sunscreen is selected from the group consisting of benzophenone-4, PABA, TEA salicylate, phenylbenzimidazole sulphonic acid and DEA methoxy cinnamate.

11. A process according to claim 1 in which the hydrophilic organic sunscreen is present in an amount of from 1 to 6 percent by weight with respect to weight of emulsion.

12. A process according to claim 1 in which an oil-in-water emulsion is formed and the emulsifier is selected from the group consisting of fatty alcohols, fatty acids, glyceryl esters, sorbitan esters, methylglycoside esters, sucrose esters, polyoxyethylene sorbitan fatty acid esters, polyoxyethylene fatty acid esters, polyoxyethylene fatty ethers, phosphate esters, fatty alcohol sulphates, polyglycoside ethers and polyglycoside esters.

13. A process according to claim 1 in which a water-in-oil emulsion is formed and the emulsifier is selected from the group consisting of silicone-based emulsifiers, ethylene oxide/propylene oxide copolymers, fatty alcohols, fatty acids, glyceryl esters, sorbitan esters, methylglycoside esters, sugar esters and alkoxylated derivatives of compounds selected from the group consisting of fatty alcohols, fatty acids, glyceryl esters, sorbitan esters, methylglycoside esters and sugar esters.

14. A process according to claim 1 in which a water-in-oil emulsion is formed in which the oil phase is non-polar and the amount of emulsifier present is less than 1 percent by weight with respect to weight of emulsion.

15. A process according to claim 1 in which a water-in-oil emulsion is formed in which non-polar oils are absent in the oil phase and the amount of emulsifier present is from 1 to 2 percent by weight with respect to weight of emulsion.

16. A process according to claim 1 in which the dispersion of particles of metallic oxide is prepared by milling the particulate metallic oxide in the oil in the presence of a particulate grinding medium and in the presence of a dispersing agent.

17. A process according to claim 16 in which the dispersion contains from 40 to 70 percent by weight metallic oxide.

18. A process according to claim 1 in which the emulsion is an oil-in-water emulsion and is formed by mixing together a hydrophobic emulsifier and oleophilic components to form an oil phase, mixing together the hydrophilic emulsifier and hydrophilic components to form an aqueous phase and subsequently mixing together the oil phase and the aqueous phase to form an oil-in-water emulsion.

19. A process according to claim 18 in which the dispersion in oil of particles of metallic oxide is added to the oil phase before the oil phase and aqueous phase are mixed.

20. A process according to claim 18 in which the dispersion in oil of particles of metallic oxide is added to the the oil-in-water emulsion.

21. A process according to claim 1 in which the dispersion of metallic oxide in oil is mixed with the emulsifier to form an oil phase and this oil phase is subsequently mixed with an aqueous phase to form a water-in-oil emulsion.

22. A process according to claim 1 in which a water-in-oil emulsion is formed and the dispersion in oil of metallic oxide is subsequently mixed with this emulsion.

23. A process according to claim 1 in which the hydrophilic organic sunscreen is added to the aqueous phase of the emulsion before this phase is mixed with the dispersion of metallic oxide in oil.

24. A process according to claim 1 in which the emulsion is prepared and the hydrophilic organic sunscreen is subsequently added to the emulsion.

25. A process according to claim 1 in which an additive selected from the group consisting of perfumes, antioxidants, moisturisers, thickeners and preservatives is added to the composition.

26. A process for the preparation of a composition suitable for topical application to human skin comprising mixing a dispersion in an oil of particles of a metallic oxide having an average particle size of less than 0.2 micrometers with one or more emulsifiers and an aqueous phase under conditions in which an emulsion is formed and with a hydrophilic organic sunscreen wherein the composition contains from 1–6%, by weight, metal oxide and from 1–6%, by weight, hydrophilic sunscreen and wherein the total sunscreen content is less than 8%.

27. A process for the preparation of a composition suitable for topical application to human skin comprising mixing together a hydrophobic emulsifier and a dispersion in oil of particles of metallic oxide having an average particle size of less than 0.2 micrometer to form an oil phase, mixing together a hydrophillic emulsifier and a hydrophillic organic sunscreen to form an aqueous phase and subsequently mixing together the oil phase and the aqueous phase under conditions in which an emulsion is formed, wherein the composition contains up to 10 percent by weight metallic oxide and up to 7 percent by weight hydrophilic sunscreen.

28. A process according to claim 27 in which the emulsion is an oil-in-water emulsion.

* * * * *